United States Patent
Jensen

(10) Patent No.: US 8,208,988 B2
(45) Date of Patent: Jun. 26, 2012

(54) SYSTEM AND METHOD FOR CONTROLLING A MEDICAL IMAGING DEVICE

(75) Inventor: Vernon Thomas Jensen, Draper, UT (US)

(73) Assignee: General Electric Company, Schenectady, NY (US)

( * ) Notice: Subject to any disclaimer, the term of this patent is extended or adjusted under 35 U.S.C. 154(b) by 2103 days.

(21) Appl. No.: 11/128,752

(22) Filed: May 13, 2005

(65) Prior Publication Data

US 2006/0293592 A1    Dec. 28, 2006

(51) Int. Cl.
*A61B 5/05*    (2006.01)
(52) U.S. Cl. .................. 600/424; 600/407; 600/427
(58) Field of Classification Search .......... 600/407, 600/424, 427
See application file for complete search history.

(56) References Cited

U.S. PATENT DOCUMENTS

| | | | |
|---|---|---|---|
| 5,255,680 A | 10/1993 | Darrow et al. | |
| 5,676,673 A | 10/1997 | Ferre et al. | |
| 5,803,089 A | 9/1998 | Ferre et al. | |
| 6,484,049 B1 | 11/2002 | Seeley et al. | |
| 6,666,579 B2 | 12/2003 | Jensen | |
| 6,823,207 B1 | 11/2004 | Jensen et al. | |
| 7,505,809 B2 | 3/2009 | Strommer et al. | |
| 2003/0149342 A1 | 8/2003 | Hanover | |
| 2006/0247521 A1* | 11/2006 | McGee | 600/434 |

FOREIGN PATENT DOCUMENTS

| | | |
|---|---|---|
| EP | 0782413 | 10/2003 |
| EP | 1583469 | 10/2005 |
| EP | 1347707 | 5/2007 |
| JP | 09512735 | 12/1997 |
| JP | 2004517670 | 6/2004 |
| JP | 2006513011 | 4/2006 |
| WO | WO9608209 | 3/1996 |
| WO | WO02056770 | 7/2002 |
| WO | WO2004062497 | 7/2004 |

OTHER PUBLICATIONS

English translation of May 8, 2009 Chinese Office Action for Chinese Application No. 200610092880.5.
Office Action from the Japan Patent Office, mailed Nov. 15, 2011, p. 1. Japanese Application No. 2006-131069.

* cited by examiner

*Primary Examiner* — Jonathan Cwern
(74) *Attorney, Agent, or Firm* — McAndrews, Held & Malloy, Ltd.; William Baxter

(57) ABSTRACT

A system and method for controlling a medical imaging device is provided. The system includes a medical imaging device. The system further includes a medical instrument. Further, the system includes a navigation subsystem that is configured to track the medical instrument. Furthermore, the system includes a control subsystem that communicates with the navigation subsystem. The control subsystem is configured to correlate at least one of orientation, position and motion of the medical instrument with a function of the medical imaging device. The control subsystem is further configured to direct the medical imaging device to perform the function associated with the medical imaging device, based on the correlation.

25 Claims, 5 Drawing Sheets

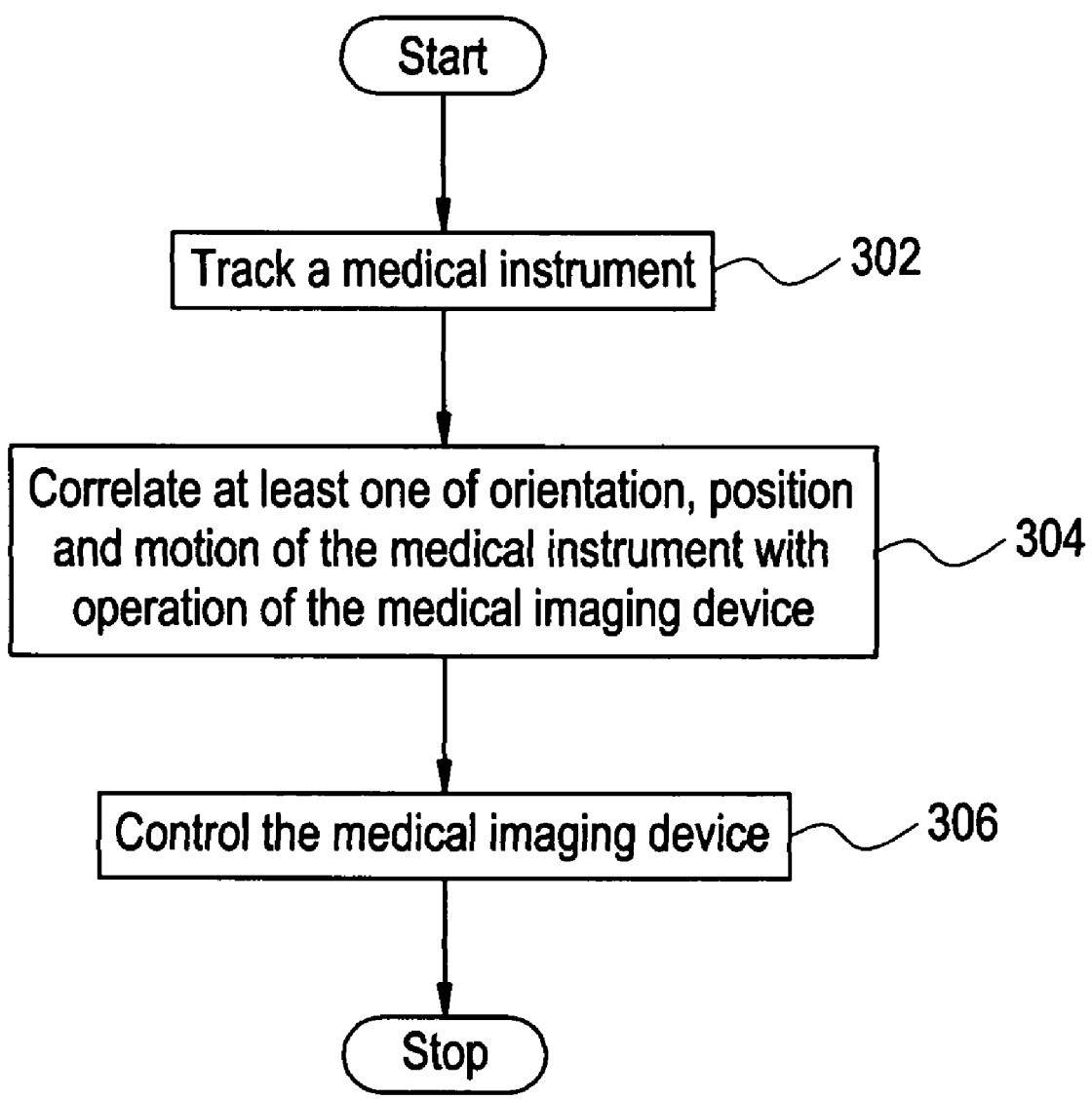

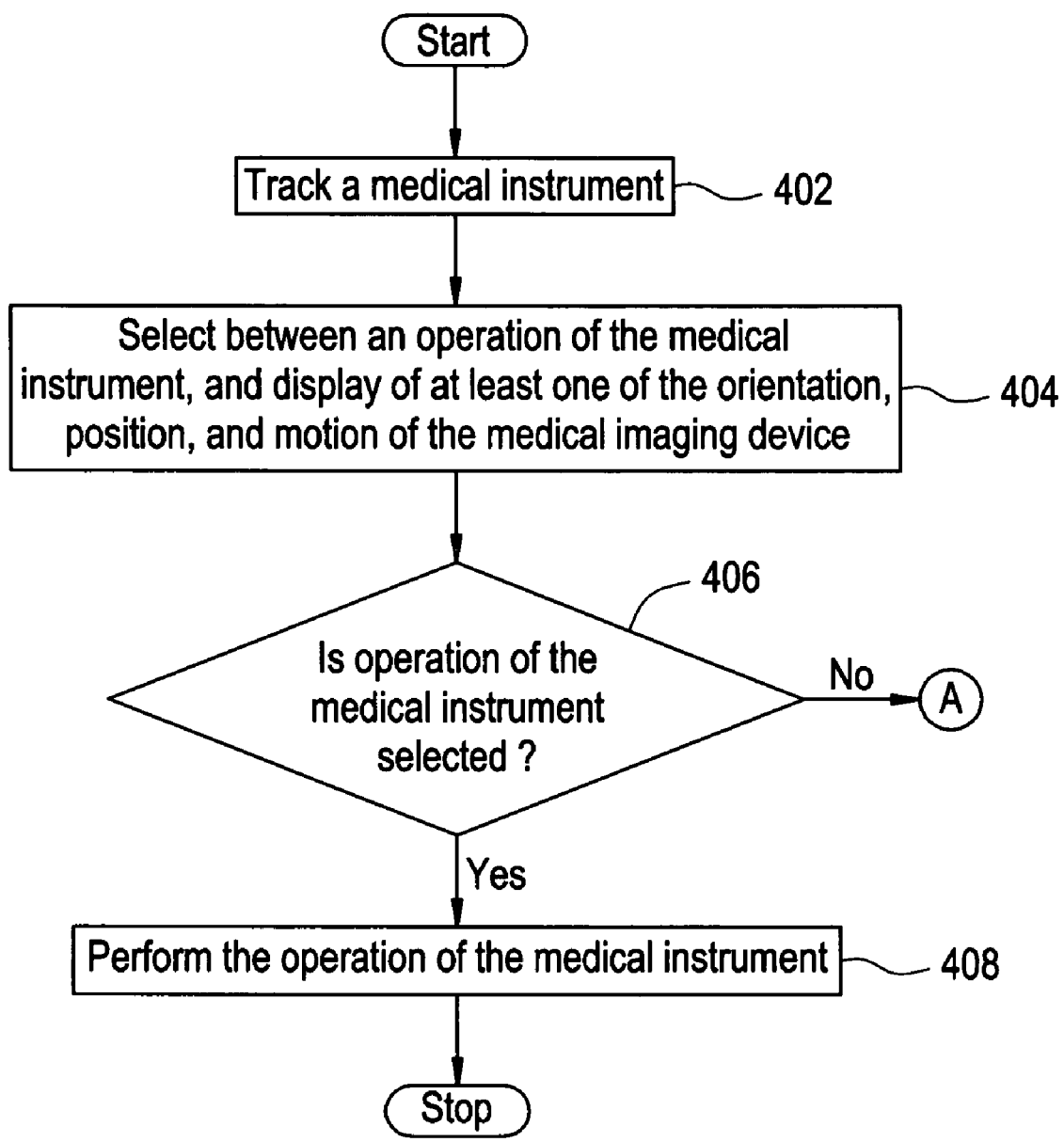

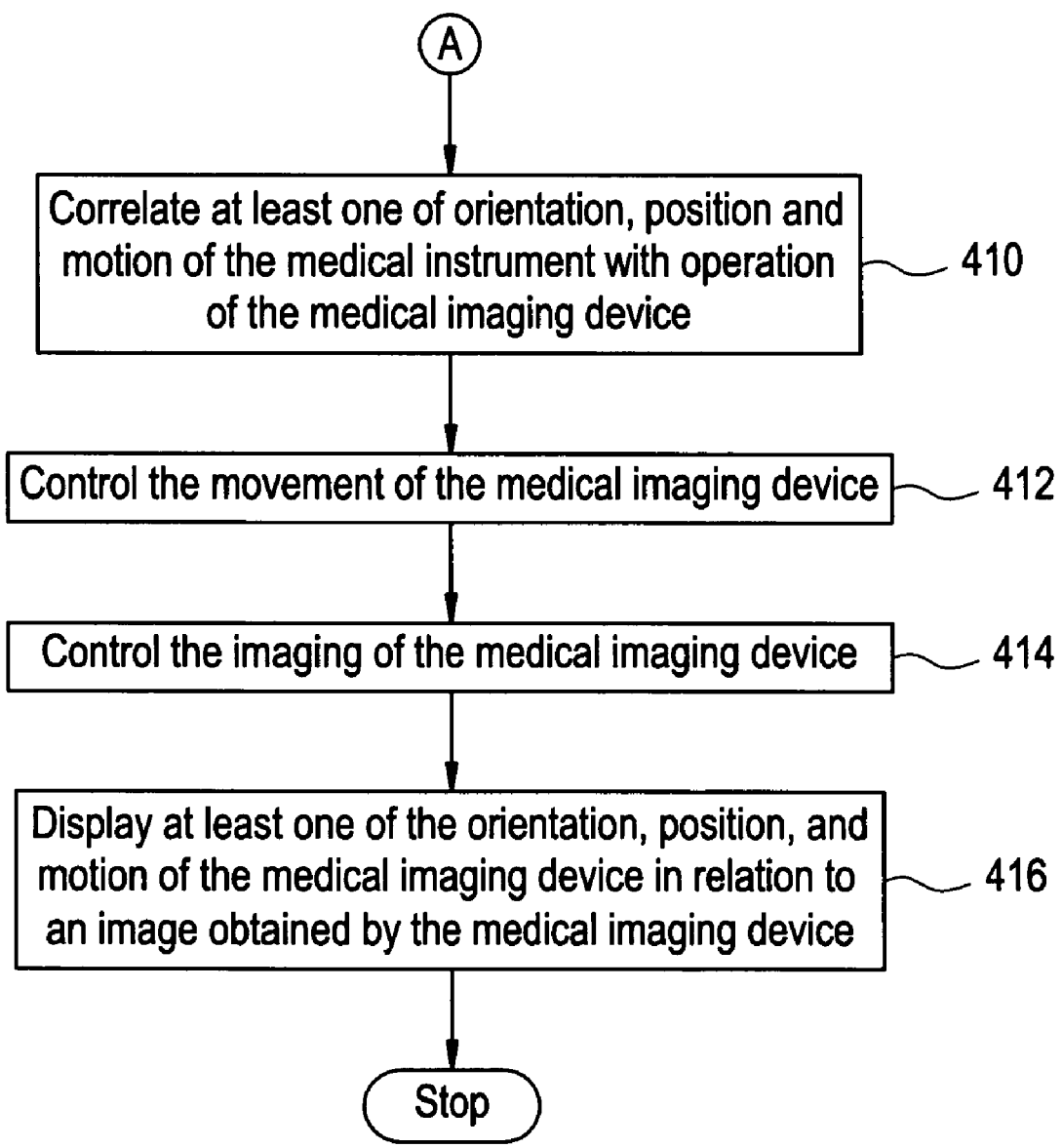

SYSTEM AND METHOD FOR CONTROLLING A MEDICAL IMAGING DEVICE

BACKGROUND OF THE INVENTION

Embodiments of the present invention generally relate to medical imaging systems, and more specifically, to systems and methods for controlling a medical imaging device.

Medical imaging techniques, including X-ray, computerized axial tomography (CAT), magnetic resonance imaging (MRI), and ultrasound are well established. With these techniques, an examining physician is provided with high-resolution images that assist the examining physician to perform subsequent detailed study and diagnosis. In a medical imaging device such as a fluoroscopic C-arm, the examining physician directs a radiation technologist to operate and position the C-arm, and subsequently acquire the high-resolution images.

Methods have evolved that provide the examining physician with a means to control the operations of the medical imaging device. For example, GE OEC 9800 MD provides the examining physician with a table-side control unit. The table-side control unit includes a positioning control that is used to position a C-arm of the GE OEC 9800 MD. Examples of positioning control include a switch, a lever, a joystick and the like. The table-side control unit therefore substitutes for the radiation technologist who operates the medical imaging device while the examining physician conducts the surgical procedure. The examining physician directs the operations of the medical imaging device by operating the table-side control unit.

In known medical devices, the examining physician depends on the radiation technologist or the table-side control unit to control the operations of the medical imaging device. This results in an interruption in the surgical procedure and may affect the results of the surgery.

Thus, a need exists for a more efficient system and method of controlling the operation of a medical imaging device. Further, a need exists for a system and method of continuously and seamlessly operating a medical device without interrupting a surgical procedure.

SUMMARY OF THE INVENTION

In one exemplary embodiment, a system for controlling a medical imaging device is provided. The system includes a medical imaging device, a medical instrument, a navigation subsystem that is configured to track the medical instrument, and a control subsystem that communicates with the navigation subsystem. The control subsystem is configured to correlate at least one of orientation, position and motion of the medical instrument with a function of the medical imaging device. The control subsystem is further configured to direct the medical imaging device to perform the function associated with the medical imaging device based on the correlation.

In another exemplary embodiment, a method for controlling a medical imaging device is provided. The method includes tracking a medical instrument, correlating at least one of orientation, position, and motion of the medical instrument with the operation of the medical imaging device, and controlling the medical imaging device, based on the correlation.

BRIEF DESCRIPTION OF THE DRAWINGS

FIG. 3 is a flowchart illustrating a method for controlling a medical imaging device, in accordance with an embodiment of the present invention.

FIG. 4A and FIG. 4B are flowcharts illustrating a method for controlling a medical imaging device, in accordance with another embodiment of the present invention.

Figure 1:
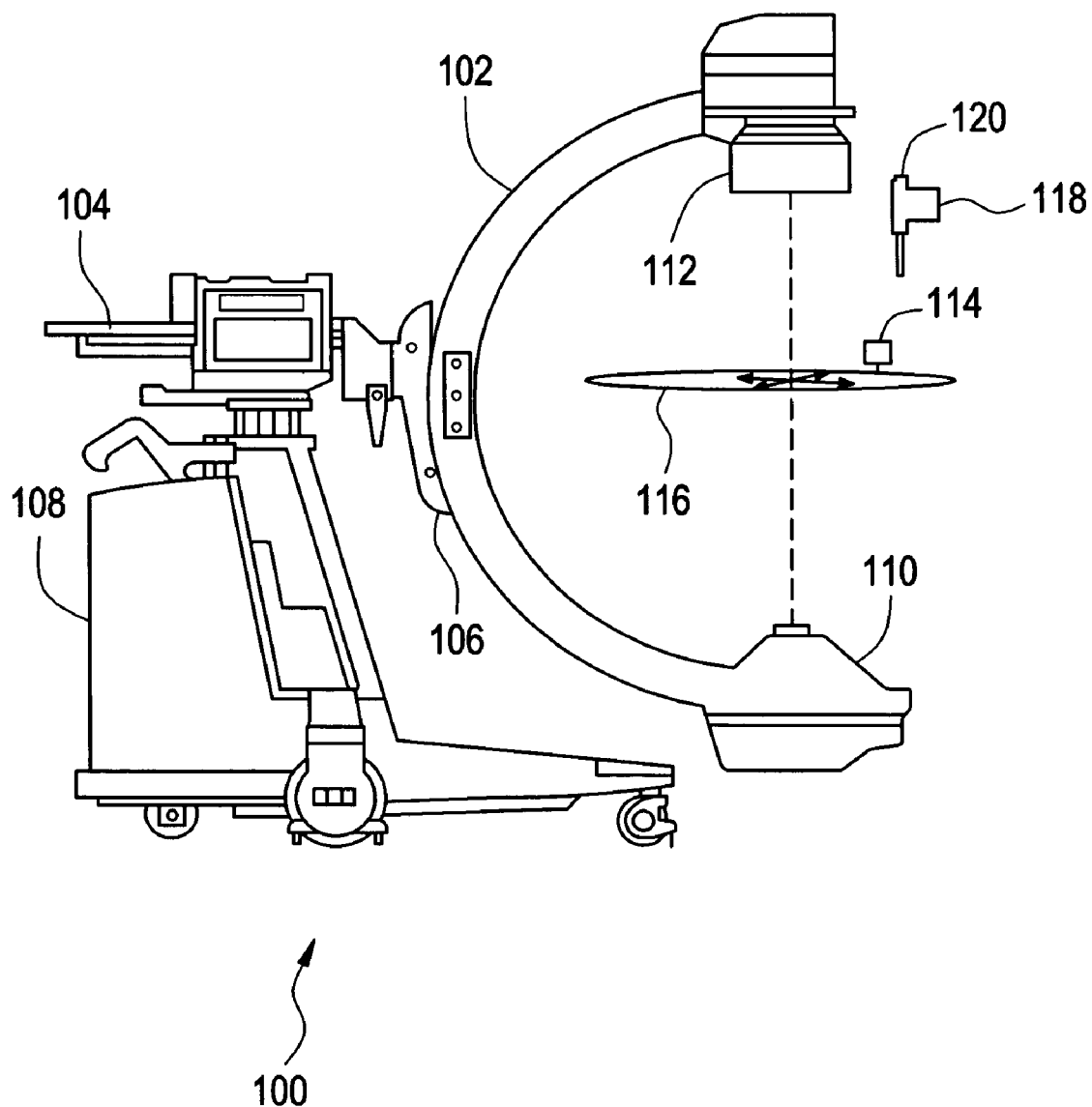
FIG. 1 illustrates a 2D fluoroscopic C-arm system, in which various embodiments of the present invention may be implemented.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings.

DETAILED DESCRIPTION OF THE INVENTION

Various embodiments of the present invention provide systems and methods for controlling a medical imaging device. The medical imaging device may be an imaging modality with a controllable gantry. Examples of such imaging modalities include a magnetic resonance imaging (MRI) system, a 2D fluoroscopic C-arm system, a 3D fluoroscopic C-arm system, a single photon emission computed tomography (SPECT) system, a computed tomography (CT) system, an optical coherence tomography (OCT) system, a positron emission tomography (PET) imaging system, an endoscope, a microscope, and so forth.

For example, embodiments of the present invention may be used with an X-ray C-arm having an X-ray source positioned on one distal end of the arm, with a detector positioned on the other distal end of the arm, such as shown and described in U.S. Pat. No. 6,104,780, entitled "Mobile bi-planar fluoroscopic imaging apparatus," U.S. Pat. No. 5,802,719, entitled "One piece C-arm for x-ray diagnostic equipment," and U.S. Pat. No. 5,627,873, entitled "Mini C-arm assembly for mobile x-ray imaging system," all of which are hereby incorporated by reference in their entireties. Optionally, the imaging system may be an MR system, such as described in U.S. Pat. No. 6,462,544, entitled "Magnetic resonance imaging apparatus," which is also hereby incorporated by reference in its entirety.

Additionally, embodiments of the present invention may also be used with Positron Emission Tomography (PET), such as shown and described in U.S. Pat. No. 6,337,481, entitled "Data binning method and apparatus for PET tomography including remote services over a network,", which is hereby incorporated by reference in its entirety, Single Photon Emission Computed Tomography (SPECT), such as shown and described in U.S. Pat. No. 6,194,725, entitled "SPECT system with reduced radius detectors," which is hereby incorporated by reference in its entirety, Electron Beam Tomography (EBT), such as shown and described in U.S. Pat. No. 5,442,673, entitled "Fixed septum collimator for electron beam tomography," which is hereby incorporated by reference in its entirety, and various other imaging systems.

Embodiments of the present invention may also be used with such navigation and tracking systems as those described in U.S. Pat. No. 5,803,089, entitled "Position Tracking and Imaging System for Use in Medical Applications," which is also hereby incorporated by reference in its entirety.

FIG. 1 illustrates a 2D fluoroscopic C-arm system 100, in which various embodiments of the present invention may be implemented. 2D fluoroscopic C-arm system 100 includes a C-arm 102. C-arm 102 has inner and outer circumferences. C-arm 102 has a uniformly circular C-shape and may alternatively comprise any arc-shaped member. C-arm 102 is held in a suspended position by support member 104, such as a structure that includes a support arm 106. Support arm 106 is mounted on a wheeled base 108. Support arm 106 enables the rotational movement of C-arm 102, for example, by means of a bearing assembly. The bearing assembly is configured between support arm 106 and C-arm 102. Support arm 106 may itself be rotatably mounted with respect to wheeled base 108. 2D fluoroscopic C-arm system 100 further includes an X-ray source 110 and an image receptor 112. In an embodiment of the present invention, image receptor 112 may be an image intensifier. Image receptor 112 includes a camera assembly. X-ray source 110 and image receptor 112 are mounted on opposite locations on C-arm 102. A high-voltage cable assembly supplies power to X-ray source 110 and image receptor 112. In addition, 2D fluoroscopic C-arm system 100 includes a tracking element 114, which serves as table or patient reference. Tracking element 114 may be rigidly attached to the patient or to table 116, on which a patient to be examined is positioned. In an embodiment of the invention, tracking element 114 may be loosely attached, for example by using a fastening tape, to the patient or to table 116. Further, a tracking element 118 is positioned at the tip of a medical instrument 120. Medical instrument 120 may be an orthopedic drill, a catheter, a surgical drill, a cutting tool, an awl, a flexible endoscope, a reamer, a scalpel, a scope, a stent, a probe, a screwdriver, and so forth. In various embodiments of the present invention, tracking elements 114 and 118 may be a transmitter and a receiver, and vice-versa.

Figure 2:
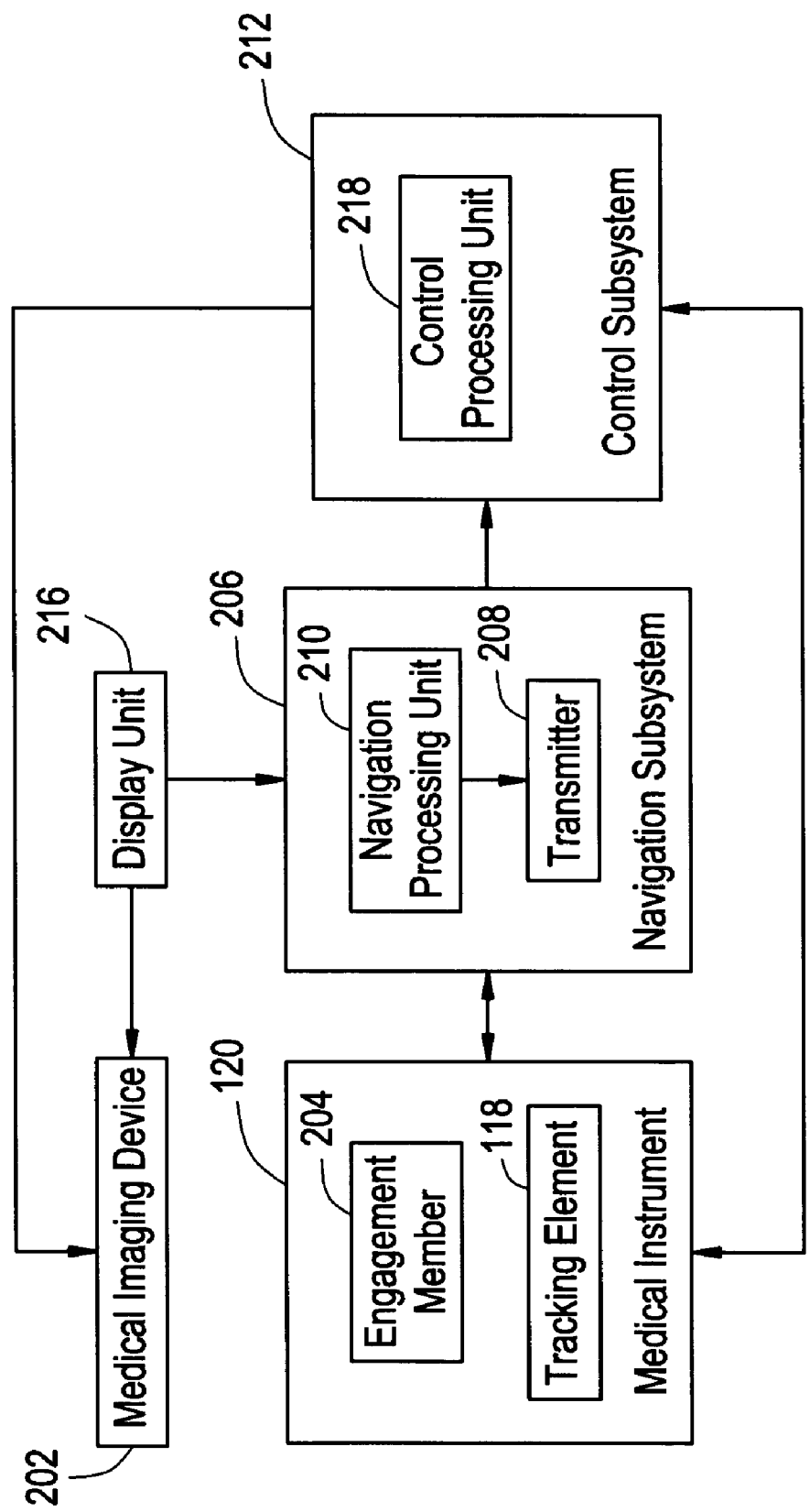
FIG. 2 illustrates a block diagram of a system for controlling a medical imaging device, in accordance with an embodiment of the present invention.

FIG. 2 illustrates a block diagram of a system for controlling a medical imaging device, in accordance with an embodiment of the present invention. The system for controlling a medical imaging device includes a medical imaging device 202, a medical instrument 120, a navigation subsystem 206, and a control subsystem 212. Medical imaging device 202 is configured to take images of an object. The object may be a heart, a vertebra, an aorta, a liver, a lung, and so forth. In an embodiment of the present invention, medical imaging device 202 may be a fluoroscopic C-arm, which includes a source and a detector.

Medical instrument 120 may be a handheld tool that is configured to perform the surgical procedures on the object, such as shown in FIG. 1. Medical instrument 120 is separate and distinct from medical imaging device 202. Medical instrument 120 may be an orthopedic drill, a catheter, a surgical drill, a cutting tool, an awl, a flexible endoscope, a reamer, a scalpel, a scope, a stent, a probe, a screwdriver, and so forth. In various embodiments of the present invention, medical instrument 120 may be a non-clinical device such as a pen, a stylus, and the like. Tracking element 118 is attached to the tip of medical instrument 120. In an embodiment of the present invention, more than one tracking element 118 may be attached to medical instrument 120. Tracking element 118 may be a small, localized element that may be positioned in or at the tip of medical instrument 120. Tracking element 118 may have a rigid or oriented housing, so that when tracking element 118 is attached to medical instrument 120, the tracked co-ordinates of tracking element 118 may yield all the co-ordinates with only a defined constant offset of medical instrument 120. To produce or detect a field that is modulated in phase, frequency or time, tracking element 118 may be energized as a field generator or sampled as a field sensor, and so forth. Therefore, some or all of the x-, y-, z-, roll-, pitch-, and yaw co-ordinates of tracking element 118 and medical instrument 120 are quickly and accurately determined. Various methods for determining x-, y-, z-, roll-, pitch-, and yaw co-ordinates are known. In another embodiment of the invention, tracking element 118 may not be attached to medical instrument 120 and may individually serve the purpose of navigation.

In various embodiments of the present invention, tracking element 118 may belong to a tracking system. Examples of a tracking system include a light-emitting diode (LED) tracking system, an optical tracking system, an ultrasound-based tracking system, an inertial position tracking system, and an acoustic-based tracking system. For example, in an embodiment of the present invention, medical instrument 120 may be a surgical drill; and tracking elements 114 and 118 may be a collection of LEDs that are positioned at the tip of the surgical drill. The positions of the LEDs on the surgical drill are detected by means of a stereo charge-coupled device (CCD) camera system. In an embodiment of the present invention, tracking elements 114 and 118 may employ a magnetic field element, which otherwise operates mainly as a point-origin field generator or field sensor. The magnetic field element may be configured with three mutually orthogonal coils.

Medical instrument 120 further includes an engagement member 204. Engagement member 204 is configured to selectively engage medical instrument 120 between a navigation function of medical instrument 120 and control of a function that is associated with the operation of medical imaging device 202. The navigation function may be at least one of orientation, position, and motion of medical instrument 120, in relation to an image that is obtained by medical imaging device 202. The function that is associated with the operation of medical imaging device 202 may be at least one movement function of medical imaging device 202 and an imaging function of medical imaging device 202. The movement function of medical imaging device 202 is limited to a plurality of known modes of motion that are performed by motorization of medical imaging device 202. Engagement member 204 communicates with at least one navigation subsystem 206, and a control processing unit 214, to perform these functions. In various embodiments of the present invention, engagement member 204 may be a button, a switch, a dial, and so forth.

Navigation subsystem 206 is configured to display the navigation function of medical instrument 120. Examples of a navigation subsystem include a light-emitting diode (LED) tracking system, an optical tracking system, an ultrasound-based tracking system, an inertial position tracking system, and an acoustic-based tracking system. Navigation subsystem 206 includes a transmitter 208 and a navigation processing unit 210. Transmitter 208 is configured to transmit a signal that is received by tracking element 120. Navigation processing unit 210 is configured to track the orientation, position and motion of medical instrument 120. Navigation processing unit 210 communicates with transmitter 208 and tracking element 118 to track the orientation, position and motion of medical instrument 120. A command protocol is established between navigation subsystem 206 and control subsystem 212. The command protocol may be a transmission control protocol with Transmission Control Protocol/Internet Protocol (TCP/IP), an I Seek You (ICQ) protocol, an Internet Relay Chat (IRC), a File Transfer Protocol (FTP) and so forth.

Control subsystem 212 includes control processing unit 214. Control processing unit 214 is configured to correlate at least one of orientation, position and motion of medical instrument 120 with the function that is associated with the operation of medical imaging device 202. Control subsystem 212 is configured to direct medical imaging device 202 to perform the function that is associated with the operation of medical imaging device 202. Control subsystem 212 directs medical imaging device 202, based on the correlation performed by control processing unit 214. Control subsystem 212 communicates with navigation subsystem 206, to perform the functions described above.

The system for controlling medical imaging device 202 further includes a display unit 216. Display unit 216 communicates with medical imaging device 202 and navigation subsystem 206, to display the image that is obtained by medical imaging device 202.

FIG. 3 is a flowchart illustrating a method for controlling a medical imaging device, in accordance with an embodiment of the present invention. At 302, a medical instrument is tracked. The medical instrument includes a tracking element that is positioned in or at the tip of the medical instrument. In an embodiment of the present invention, the medical instrument may include more than one tracking element. The tracking element sends one or more signals to a transmitter. The transmitter receives the signal and tracks the medical instrument.

At 304, at least one of orientation, position and motion of the medical instrument is correlated with the operation of the medical imaging device. The medical instrument includes an engagement member. The engagement member selectively engages the medical instrument between a navigation function and control of a function that is associated with the operation of the medical imaging device. The navigation function and the function that is associated with the operation of the medical imaging device have been described in conjunction with FIG. 2.

At 306, the medical imaging device is controlled. The function that is associated with the operation of the medical imaging device is controlled, based on the correlation of at least one of orientation, position, and motion of the medical instrument with the operation of the medical imaging device. In an embodiment of the present invention, the movement function of the imaging device is controlled. In another embodiment of the present invention, the imaging function of the medical imaging device is controlled.

In an embodiment of the present invention, the medical imaging device may be a fluoroscopic C-arm system, which includes a source and a detector. The medical instrument may be an orthopedic drill. The engagement member may be a push button located on the orthopedic drill. The push button controls the movement function of the fluoroscopic C-arm system. For example, if the push button is pressed twice quickly, a signal is transmitted, to control the movement of the fluoroscopic C-arm system. Further, if the push button is pressed continuously, the orthopedic drill operates as a joystick to direct the movement of the fluoroscopic C-arm system. At least one of orientation, position and motion of the orthopedic drill directs the movement of the fluoroscopic C-arm system. For example, if the orthopedic drill is rotated around the space of the orthopedic drill, a signal is transmitted, which directs the fluoroscopic C-arm system to follow the direction or orientation of the orthopedic drill. Further, if the push button is pressed again, or released, a signal is transmitted to direct the fluoroscopic C-arm system to cease the movement function.

FIG. 4A and FIG. 4B are flowcharts illustrating a method for controlling a medical imaging device, in accordance with another embodiment of the present invention. At 402, the medical instrument is tracked by at least one tracking element that is positioned in or at the tip of the medical instrument. At 404, a selection is made between the operation of the medical instrument, and the display of at least one of orientation, position and motion of the medical instrument, in relation to an image that is obtained by the medical imaging device. The operation of the medical instrument refers to a surgical procedure that is performed on the patient with the medical instrument. Examples of surgical operations include drilling, cutting, exploring cavities, punching, and so forth. The selection is made through an engagement member. For example, the medical imaging device is a fluoroscopic C-arm system, the medical instrument is an orthopedic drill, and the engagement member is a push button. If the examining physician presses the push button twice quickly, a signal is transmitted. This signal signifies that the orthopedic drill operates as a joystick, to control the movement of the fluoroscopic C-arm system. Appropriate movement of the fluoroscopic C-arm results in the proper positioning of the C-arm. Proper positioning of the C-arm assists in the display of at least one of orientation, position, and motion of the orthopedic drill, in relation to the image that is obtained by the fluoroscopic C-arm system. If the examining physician presses the button once, a different signal is transmitted, which signifies that the orthopedic drill will not operate as the joystick, and will operate as a tool to conduct the surgical procedure.

At 406, a check is conducted if the operation of the medical instrument is selected. If operation of the medical instrument is selected, then at 408, the operation of the medical instrument is performed, to conduct the surgical procedure. If the operation of the medical instrument is not selected, then at 410, at least one of orientation, position and motion of the medical instrument, in relation to the image that is obtained by the medical imaging device, is selected. At 412, the movement of the medical imaging device is controlled. In an embodiment, the medical imaging device is a fluoroscopic C-arm system, the medical instrument is an orthopedic drill, and the engagement member is a push button. For example, if the orthopedic drill is rotated around the space of the orthopedic drill, a signal is transmitted, which directs the fluoroscopic C-arm system to follow the direction or orientation of the orthopedic drill. In another example, if the orthopedic drill is tipped in a direction, a signal is transmitted, which directs the fluoroscopic C-arm system to move the orbital rotation of the C-arm in the direction in which the orthopedic drill is tipped.

At 414, imaging of the medical imaging device is controlled. After the medical imaging device is moved to an appropriate position to examine the anatomy of the patient, and conduct the surgery, the medical imaging device acquires the image of the patient.

At 416, at least one of orientation, position and motion of the medical instrument is displayed in relation to the image that is obtained by the medical imaging device. In an embodiment, the medical imaging device is a fluoroscopic C-arm system, and the medical instrument is an orthopedic drill. The image that is obtained by the fluoroscopic C-arm displays at least one of orientation, position and motion of the orthopedic drill in relation to the anatomy of the patient. By viewing the image, the examining physician is able to determine the precise location of the orthopedic drill on the patient and continue the surgical procedure.

Various embodiments of the present invention provide a medical imaging system that enables the examining physician to control C-arm positioning from within the sterile field, without the use of additional hardware. Further, the various embodiments of the present invention provide a medical imaging system that enables tracking of medical instruments, and subsequently controls the operations of the medical imaging devices by means of at least one of orientation, position and motion of the medical instruments.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

What is claimed is:

1. A system for controlling a medical imaging device, comprising:
    a medical imaging device;
    a medical instrument having at least one tracking element, said medical instrument selectively engageable between a navigation function and a control function that is associated with operation of said medical imaging device;
    a navigation subsystem comprising (i) a transmitter adapted to transmit a signal that is received by said tracking element; and (ii) a navigation processing unit in communication with said transmitter and said at least one tracking element in order to track the orientation, position, and motion of said medical instrument; and
    a control subsystem in communication with said navigation subsystem, said control subsystem having a control processing unit that is operable to correlate at least one of the orientation, position, and motion of said medical instrument with a function associated with operation of said medical imaging device when said medical instrument operates in the control function, said control subsystem also being operable to direct said medical imaging device to perform the function associated with operation of said medical imaging device based on at least one of the orientation, position, and motion of said medical instrument.

2. The system of claim 1, wherein the function associated with operation of said medical imaging device includes at least one of a movement function and an imaging function of said medical imaging device.

3. The system of claim 1, further comprising a display unit in communication with said medical imaging device and said navigation subsystem, wherein said navigation subsystem is adapted to display the navigation function of said medical instrument, wherein the navigation function includes at least one of the orientation, position, and motion of said medical instrument in relation to an image obtained by said medical imaging device.

4. The system of claim 3, wherein said medical instrument further comprises an engagement member that is in communication with at least one of said navigation and control processing units, said engagement member being configured to selectively engage said medical instrument between the navigation function and the control function associated with operation of said medical imaging device.

5. The system of claim 4, wherein said engagement member comprises at least one of a button, switch, and dial.

6. The system of claim 1, wherein said medical imaging device is a fluoroscopic C-arm comprising a source and a detector.

7. The system of claim 1, wherein said medical instrument is a handheld medical instrument comprising at least one of a probe, surgical drill, cutting tool, and scope.

8. The system of claim 1, wherein said navigation subsystem is one of an ultrasound, inertial position, optical and electromagnetic navigation subsystem.

9. The system of claim 1, wherein said medical instrument operates as a joystick to direct movement of the medical imaging device in the control function.

10. A method of controlling a medical imaging device, comprising:
    tracking a medical instrument;
    using a processing unit to correlate orientation, position and motion of the medical instrument with operation of the medical imaging device; and
    controlling the medical imaging device based on said correlating,
    wherein said controlling comprises operating the medical instrument as a joystick to direct movement of the medical imaging device.

11. The method of claim 10, wherein said tracking comprises tracking the medical instrument with one of an ultrasound, inertial position, optical and electromagnetic navigation subsystem.

12. The method of claim 10, wherein said controlling comprises at least one of moving the medical imaging device and imaging with the medical imaging device.

13. The method of claim 10, further comprising displaying at least one of the orientation, position, and motion of the medical instrument in relation to images obtained by said medical imaging device.

14. The method of claim 13, further comprising selecting between said controlling and said displaying.

15. A system for controlling a medical imaging device, comprising:
    a medical imaging device;
    a medical instrument;
    a navigation subsystem configured to track said medical instrument; and
    a control subsystem in communication with said navigation subsystem, said control subsystem being operable to control all movement and imaging functions of said medical imaging device through said medical instrument.

16. The system of claim 15, wherein said navigation subsystem is configured to track at least one of an orientation, position, and motion of said medical instrument; and said control subsystem being operable to control said medical imaging device based on at least one of the orientation, position, and motion of said medical instrument.

17. The system of claim 15, wherein said control subsystem is operable to control at least one of a movement function and an imaging function of the medical imaging device.

18. The system of claim 15, further comprising a display unit in communication with said medical imaging device and said navigation subsystem, wherein said navigation subsystem is adapted to display at least one of an orientation, position, and motion of said medical instrument in relation to an image obtained by said medical imaging device.

19. The system of claim 18, wherein said medical instrument further comprises an engagement member that is in communication with at least one of said navigation and control subsystems, said engagement member being configured to selectively engage said medical instrument between navigation and medical imaging device control functions.

20. The system of claim 19, wherein said engagement member comprises at least one of a button, switch, and dial.

21. The system of claim 19, wherein the navigation function includes at least one of the orientation, position, and motion of said medical instrument in relation to an image obtained by said medical imaging device.

22. The system of claim 15, wherein said medical imaging device is a fluoroscopic C-arm comprising a source and a detector.

23. The system of claim 15, wherein said medical instrument is a handheld medical instrument comprising at least one of a probe, surgical drill, cutting tool, and scope.

24. The system of claim 15, wherein said navigation subsystem is one of an ultrasound, an inertial position, optical and electromagnetic navigation subsystem.

25. The system of claim 15, wherein said medical instrument operates as a joystick to direct movement of the medical imaging device.

* * * * *